United States Patent [19]

Penny

[11] Patent Number: 4,702,849
[45] Date of Patent: Oct. 27, 1987

[54] METHOD OF INCREASING HYDROCARBON PRODUCTION FROM SUBTERRANEAN FORMATIONS

[75] Inventor: Glenn S. Penny, Duncan, Okla.
[73] Assignee: Halliburton Company, Duncan, Okla.
[21] Appl. No.: 834,171
[22] Filed: Feb. 25, 1986
[51] Int. Cl.[4] ............................................. E21B 43/26
[52] U.S. Cl. ............................ 252/8.554; 166/308; 252/8.551; 260/502.4 P
[58] Field of Search .................... 252/8.551, 8.554; 166/308

[56] References Cited

U.S. PATENT DOCUMENTS

| | | | |
|---|---|---|---|
| 2,765,851 | 10/1956 | Bond ................................. | 252/8.554 |
| 2,908,643 | 10/1959 | Thompson et al. .............. | 252/8.554 |
| 3,269,812 | 8/1966 | Irani et al. ....................... | 252/153 X |
| 3,288,846 | 11/1966 | Irani et al. ....................... | 252/180 X |
| 4,322,306 | 3/1982 | Dill ................................. | 252/8.551 X |
| 4,425,242 | 1/1984 | Penny et al. ..................... | 252/8.551 |

Primary Examiner—Herbert B. Guynn
Attorney, Agent, or Firm—Robert A. Kent

[57] ABSTRACT

A method of treating a carbonate-containing subterranean formation to increase the production of hydrocarbons therefrom. The formation is contacted with an aqueous solution of one or more of certain anionic aminophosphonate compounds whereby the composition is caused to be absorbed onto the solid surfaces present in the subterranean limestone-containing formation and substantially reduces the tendency of such surfaces from becoming water or hydrocarbon wet.

9 Claims, 1 Drawing Figure

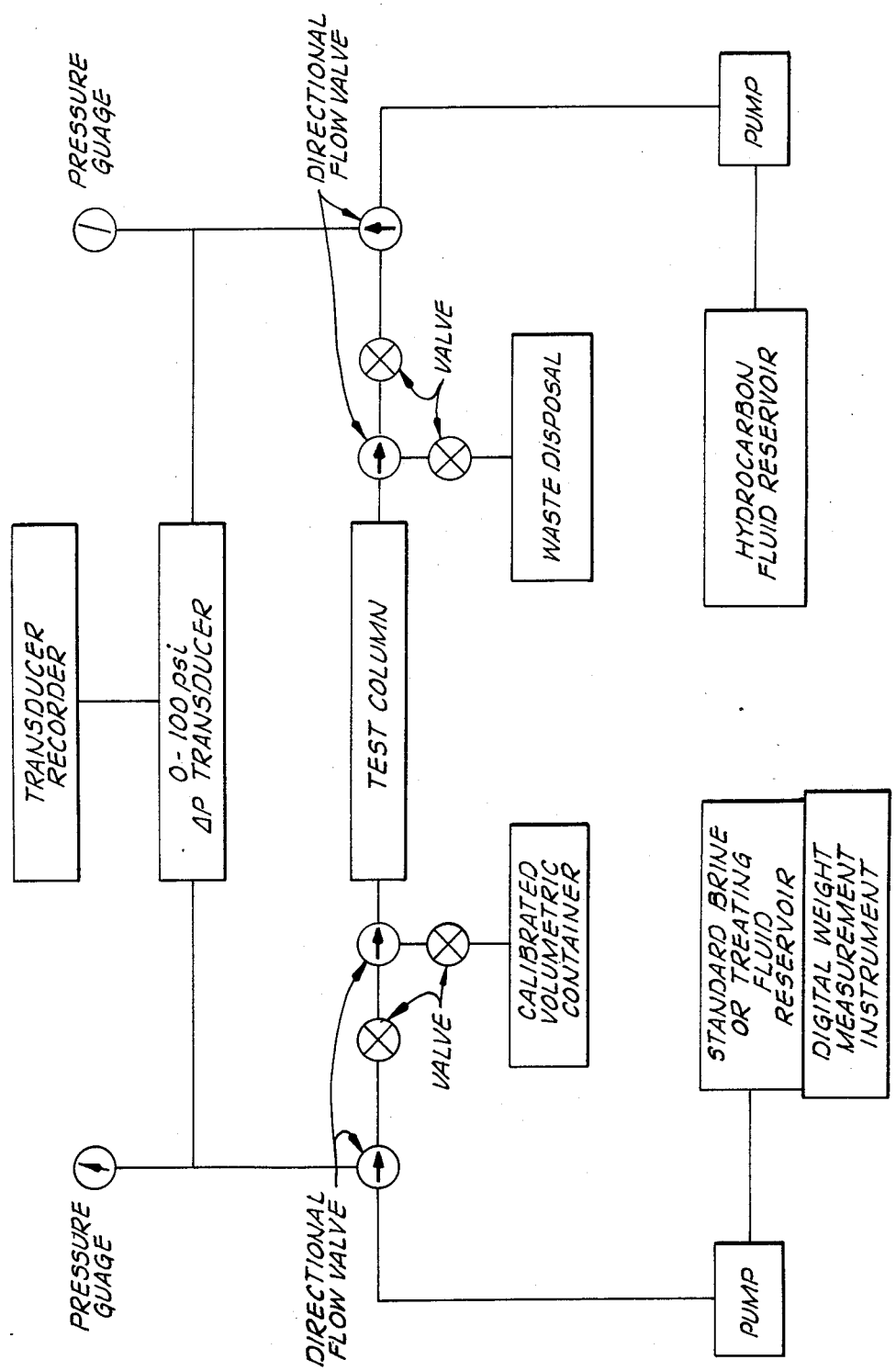

METHOD OF INCREASING HYDROCARBON PRODUCTION FROM SUBTERRANEAN FORMATIONS

Various procedures have been developed and utilized heretofore to increase the flow of hydrocarbons from hydrocarbon-containing subterranean formations penetrated by well bores. For example, a commonly used production stimulation technique involves creating and extending fractures in the subterranean formation to provide flow channels therein through which hydrocarbons flow from the formation to the well bore. The fractures are created by introducing a fracturing fluid into the formation at a flow rate which exerts a sufficient pressure on the formation to create and extend fractures therein. Solid fracture proppant materials, such as sand, are commonly suspended in the fracturing fluid so that upon introducing the fracturing fluid into the formation and creating and extending fractures therein, the proppant material is carried into the fractures and deposited therein whereby the fractures are prevented from closing due to subterranean forces when the introduction of the fracturing fluid has ceased.

In such formation fracturing and other production stimulation procedures, it is important to leave the formation with maximum permeability or conductivity whereby hydrocarbons contained in the formation flow to the well bore with the least possible restriction. In order to achieve maximum conductivity of hydrocarbons from subterranean formations, whether or not such formations have been fractured or otherwise stimulated, it has heretofore been the practice to cause the formation surfaces to be water wet. Such water wetting has been shown to provide an improved flow of hydrocarbons through flow channels and capillaries in the magnitude of about three times greater than when the formation surfaces are hydrocarbon wet.

The water wetting of solid surfaces in subterranean hydrocarbon-containing formations as well as the surfaces of solid proppant material deposited therein has heretofore been accomplished using surfactants whereby a layer of water or water and surfactant is spread over the solid surfaces. Such layers of water or water and surfactant are extremely viscous near the interface of the layer and the solid surface, and while the layer provides a slippage or lubricating effect at the interface thereof with hydrocarbons which decreases the resistance to flow, the layer reduces the effective diameter of capillaries and flow channels. This reduction of effective diameter restricts fluid flow, and in very small capillaries or flow channels becomes significant, that is, when the capillary radius is equal to the viscous wetting layer thickness, the flow of hydrocarbons is blocked by the layer.

SUMMARY OF THE INVENTION

By the present invention, methods are provided whereby certain compounds are caused to be adsorbed onto solid surfaces and particularly surfaces of carbonate materials in subterranean hydrocarbon-containing formations in a very thin layer, that is, a layer which is preferably one molecule thick and significantly thinner than a layer of water or a water-surfactant mixture. The compounds so adsorbed on the surfaces resist or substantially reduce the wetting of the surfaces by water and hydrocarbons and provide high interfacial tensions between the surfaces and water and hydrocarbons This allows the hydrocarbons to displace injected water leaving a lower water saturation and an increased flow of hydrocarbons through capillaries or flow channels in the formations.

BRIEF DESCRIPTION OF THE DRAWING

The single figure is a diagrammatic illustration of the test apparatus employed in evaluating the performance of various compositions in increasing hydrocarbon production.

DESCRIPTION OF PREFERRED EMBODIMENT

The compounds which are utilized in accordance with the methods of this invention to reduce the tendency of limestone surfaces from becoming water or hydrocarbon wet while not creating significantly thick and/or viscous layers thereon are certain anionic alkyl polyamine and anionic perfluoro compounds and mixtures of such compounds or salts thereof represented by the formula:

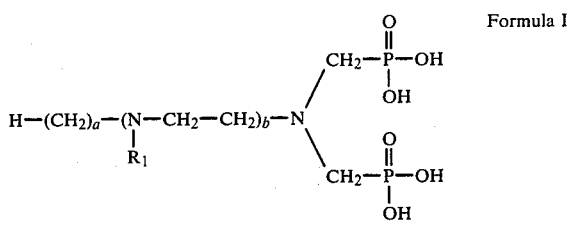

Formula I

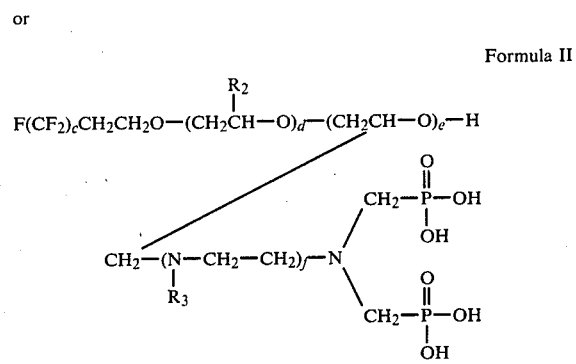

Formula II wherein a is a whole number or fraction thereof in the range of from about 4 to about 18;

wherein b is a whole number or fraction thereof in the range of from about 0 to about 5;

wherein c is a whole number or fraction thereof in the range of from about 4 to about 18;

wherein d is a whole number or fraction thereof in the range of from about 0 to about 29;

wherein e is a whole number or fraction thereof in the range of from about 1 to about 3;

wherein f is a whole number or fraction thereof in the range of from about 0 to about 9;

$R_1$ is independently selected from the group consisting of hydrogen, an alkyl radical such as a methyl group or the like or methyl phosphonate;

$R_2$ is independently selected from the group consisting of hydrogen, a methyl group and an ethyl group; and $R_3$ is independently selected from the group consisting of hydrogen, an alkyl radical such as a methyl group or the like or methyl phosphonate.

The phrase "whole number or fraction thereof" as used herein indicates that the formula may represent an admixture of compounds wherein the average values of a and b or c, d, e and f can be any number in the range set forth such as 2 or 8 or 10 or a fraction such as 2.1, 8.5, 8.8 or 10.2 and the like.

Preferably, in the above formulas, a is in the range of from about 8 to about 10;

b is in the range of from about 1 to about 3;
c is in the range of from about 6 to about 12;
d is in the range of from about 1 to about 25;
e is in the range of from about 1 to about 2;
f is in the range of from about 1 to about 6;
$R_1$ and $R_3$ are independently selected from hydrogen and methyl radicals; and
$R_2$ is independently selected from the group consisting of hydrogen and methyl radicals.

The preferred perfluoronated compound for use in accordance with the present invention is that represented by the following formula:

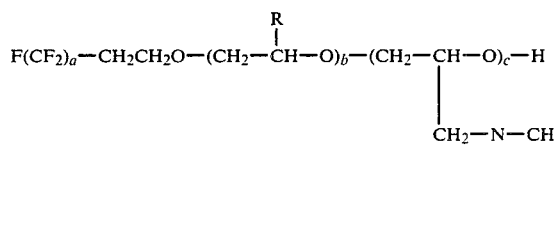

In this preferred perfluoronated compound, a is a whole number or fraction thereof in the range of from about 6 to about 12;

b is a whole number or fraction thereof in the range of from about 10 to about 25;
c is a whole number or fraction thereof in the range of from about 1 to about 2; and
R is independently selected from hydrogen and methyl radicals.

Of this group of compounds, the most preferred is where a is a whole number or fraction thereof in the range of from about 7 to about 9 and, most preferably, about 8;

b is a whole number or fraction thereof in the range of from about 15 to about 25;
c is a whole number or fraction thereof in the range of from about 1 to about 3;
R is independently selected from hydrogen and methyl radicals, preferably, at least 15 of said R being hydrogen.

In carrying out the methods of the present invention, the anionic alkyl polyamine compound or anionic perfluoro compound or compounds and their salts can be applied directly to a subterranean formation whereby the surfaces thereof are contacted by the compounds and adsorbed thereon. Preferably, the anionic compound or compounds utilized are dissolved or dispersed in a carrier fluid which is in turn introduced into the formation whereby the carried anionic perfluoro compounds are distributed in the formation and contact solid surfaces therein whereby they are adsorbed thereon. Aqueous or hydrocarbon base carrier fluids can be utilized in the form of liquids, foams, emulsions and so forth. The aqueous fluid can comprise, for example, salt solutions such as KCl, $NH_4Cl$ or NaCl or fresh water. The carrier fluid also can contain other conventional additives which are compatible with the anionic compound of the present invention, such as, for example, nonemulsifying agents or surface tension reducing agents, mutual solvents, corrosion inhibitors, gelling agents, paraffin and iron control agents and the like. The particular quantity of anionic compounds combined with the carrier fluid can vary widely depending upon the type of formation to be treated and other factors, but generally the anionic compounds utilized are combined with the carrier fluid in an amount in the range of from about 0.01% to about 0.5% by weight of the carrier fluid. It is to be understood that larger quantities can be employed but such use is economically undesirable.

In carrying out subterranean formation fracturing processes wherein a fracturing fluid is introduced into a subterranean, limestone or limestone-containing formations at a rate such that fractures are created in the formation and extended therein, the anionic compound

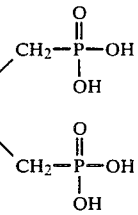

Formula III or compounds utilized are conveniently combined with the fracturing fluid prior to introducing it into the formation.

In the usual case, a non-viscous preflush solution is injected into the formation, followed by a viscous fracturing fluid without proppant material which is in turn followed by a viscous fracturing fluid carrying solid proppant material, such as sand, bauxite, glass beads or the like. The fracturing fluids create and extend fractures in the formation and the solid proppant material is carried into and deposited in the fractures. In carrying out such fracturing procedures in accordance with this invention, the anionic compound or compounds utilized can be dissolved or dispersed in the non-viscous preflush solution as well as the viscous fracturing fluids in a convenient manner. Upon introducing the preflush and fracturing fluids into the subterranean formation, the anionic compounds are adsorbed on the solid surfaces of the formation. Thus, the carbonate-containing surfaces of the formation have anionic alkyl polyamines or perfluoro compounds adsorbed thereon whereby such surfaces are substantially prevented from being wetted by water or hydrocarbons and the flow of hydrocarbons through the formation is significantly increased.

In subterranean formation fracturing procedures, cationic perfluoro compounds discussed in U.S. Pat. No. 4,425,242 can be combined with the proppant-laden fluids introduced into the formation in a sufficient quantity whereby the compounds are adsorbed on the proppant material employed if such proppant material has not been pretreated. This quantity can vary depending upon the type of formation and the quantity of proppant material utilized, but generally is in the range of from about 0.01% to about 0.2% by weight of the fracturing fluid and proppant material used.

The Starting Amine Compounds

The starting amines of Formula I may be prepared by any of the various known methods. In one method, the amines may be prepared by ammonolysis of various alkyl halides utilizing the following reaction conducted while heating the reactants under pressure:

$$RX + NH_3 \rightarrow RNH_3 + X^-$$

wherein R has the formula $H\text{-}(CH_2)_a$. The free amine may be obtained by treating the salt with sodium hydroxide or another hydroxide ion source to yield a compound having the formula:

$$H\text{-}(CH_2)_a\text{-}NH_2 \qquad \text{Formula IV}$$

The diamines to pentamines may be produced by the reaction sequence having the formula:

$$XCH_2CH_2X + 4NH_3 \rightarrow H_2NCH_2CH_2NH_2 + 2NH_4$$

further reaction with ethylene halide and ammonia gives the co-products diethylenetriamine, triethylenetetramine and tetraethylenepentamine. This product then is reacted with an appropriate alkyl halide to yield a product having the formula:

$$\underset{|}{H\text{—}(CH_2)_a\text{—}(\overset{R}{N}CH_2CH_2)_b\text{—}NH_2} \qquad \text{Formula V}$$

The subscripts in Formulas IV and V having the numerical values previously indicated in Formula I.

The foregoing chemicals are commercially manufactured by well known procedures and are known to be utilized in the manufacture of adhesives, dewatering agents, polymerized resins, crosslinking agents and the like.

The Starting Perfluoro Alcohol Compounds

The starting perfluoro compounds which are used to generate perfluoronated substituents within the compositions of this invention are derived from perfluoro substituted ethanols which are represented by the following formula:

$$F(CF_2)_aCH_2CH_2OH \qquad \text{Formula VI}$$

In the above Formula VI, a has the numerical values previously indicated in Formulae II and III. A preferred per fluoro ethanol is commercially obtained from E. I. duPont de Nemours & Co. under the commercial name "Zonyl BA". This material is generally described by Formula IV wherein a is from about 6 to about 12 and wherein the average a is equal to about 8. An average a, again, indicates that the compounds used may be an admixture of molecules wherein a is individually 6, 8, 10 or 12 and the like with the numerical average being about 8.

The Oxiranes and Substituted Oxiranes

The starting oxirane and substituted oxirane used to initially react with the perfluoronated alcohols previously described are chosen from the group consisting of ethylene oxide, propylene oxide, butylene oxide and mixtures thereof. The preferred oxirane reactants are chosen from the group consisting of ethylene oxide, propylene oxide and mixtures thereof added sequentially or via mixed addition. The most preferred oxirane reactant is propylene oxide.

The Epihalohydrins

The starting epihalohydrins used to react with the perfluoronated alcohol adducts with the oxirane compounds previously described are chosen from the group consisting of epichlorohydrin, epibromohydrin and epiiodohydrin. The preferred epihalohydrin is epichlorohydrin.

The Amines

The starting compounds used to form the perfluoro-substituted compounds of Formula II of the present invention can comprise, for example, ammonia, primary amines, polyamines or the like which when reacted with the epihalohydrin forms a perfluoro-substituted amine.

The Catalysts

The catalysts used in the reactions of the perfluoro alcohol previously described, the oxirane and substituted oxirane compounds previously described, and the epihalohydrins described above are chosen from Lewis acid compounds. These catalysts are represented by antimony pentachloride, boron trichloride, boron trifluoride, stannic chloride, ferric and ferrous chloride and the like. The Lewis acid preferred in both the reaction between the perfluoro alcohol and the oxirane compounds, as well as between the alkoxylate adduct formed by this first reaction and the epihalohydrin is antimony pentachloride. The catalyst is used at a concentration ranging from 0.01% based on the final adduct up to about 1.0% by weight based on the final adduct weight. A preferred range of catalyst is between 0.1% and 0.5% by weight based on the final adduct. A most preferred catalyst concentration, particularly in reference to the use of antimony pentachloride is between 0.2 and 0.4% by weight of the final adduct obtained from this combined reaction.

Reaction Conditions, Synthesis of Perfluoro Alcohol/Oxirane Compounds

The initial alkoxylate adducts required to manufacture the compounds of this invention are synthesized by reacting the perfluoro alcohol described above with the oxirane and substituted oxirane compounds described above. This first reaction is done under anhydrous conditions and is catalyzed by a Lewis acid catalyst, again described above. After this initial alkoxylate adduct is formed, it is then reacted with an epihalohydrin to obtain the final adduct.

The reaction of the perfluoro alcohol with the oxirane and substituted oxiranes is accomplished by using the following method or variations thereof.

To an autoclave which has previously been charged with the perfluoro alcohol and a Lewis acid catalyst, an amount of an oxirane or substituted oxirane or a mixture thereof is added at such a rate so as to maintain a reaction temperature between 60° and 140° C. The reaction is catalyzed by a Lewis acid, preferably antimony pentachloride, and additional catalyst may be added simultaneously with the addition of the oxirane/substituted oxirane compounds. The oxirane/substituted oxirane compounds may be added in such quantities such that the molar ratio of perfluoro alcohol to oxirane/substituted oxirane compounds is between 1:4 and 1:10, and a most preferred molar ratio is between 1:6 and 1:8. The reaction rate may be controlled by using a combination of temperature and catalyst concentration variations.

Once the oxirane/substituted oxirane compounds are completely charged to the autoclave, the autoclave is maintained at a temperature of at least 80° C. until the reaction is completed. It is preferred that the autoclave be maintained at temperatures of at least 100° C. for a time period of at least 30 minutes following the completed addition of the oxirane/substituted oxirane chosen. The autoclave may be cooled and a sample may be removed for analysis or for further chemical reaction. Additional oxirane/substituted oxirane also may be charged to the autoclave to obtain higher molecular ratios of perfluoro alcohol and oxirane/substituted oxirane or to vary the type of oxirane/substituted oxirane substitution in the final product. The reaction may be conveniently monitored by analyzing unreacted oxiranes using Gas Chromatographic techniques. The most preferred adduct is obtained when residual oxirane levels are about 0.2 weight percent or below.

Alternatively, the autoclave may be maintained at reaction temperature while additional catalyst and the epihalohydrin chosen to obtain the final adduct is added to the autoclave contents. The preferred final adduct is again obtained when residual epihalohydrin levels are about 0.2 weight percent or below as is conveniently monitored by using Gas Chromatographic techniques. All of the above reactions are anhydrous in nature and are accomplished in an inert atmosphere such as is obtained by a nitrogen environment.

Reaction Conditions; Synthesis of Perfluoro Alcohol/Oxirane-Substituted Oxirane/Epihalohydrin Adduct Once the initial alkoxylated adduct is formed using reaction conditions described above, or variations thereof, the autoclave may be cooled and the initial alkoxylated adduct removed for further reactions. As above, the initial adduct may be reacted with quantities of epihalohydrin such that the desired molar ratios represented in Formula I and II above may be obtained. Again, reaction conditions are anhydrous, in an inert environment such as may be obtained with a nitrogen atmosphere, under Lewis acid catalyst conditions previously described, and are best obtained by the addition of the chosen epihalohydrin, such as epichlorohydrin, to an autoclave containing the previously reacted compound derived from the reaction of perfluoro alcohol and the oxirane/substituted oxirane compounds.

The reaction temperatures are preferably maintained below 120° C. and the Lewis acid catalyst is preferably used at a concentration of at least 0.1% based on the weight of the expected final product. The preferred catalyst is, again, antimony pentachloride, although $BF_3$ etherate also may be readily used. The antimony pentachloride gives fewer side reaction products and is most preferred as a catalyst for this reaction.

The addition of epihalohydrin is maintained at a rate to control the reaction temperature below 120° C., preferably within a range between 60° and 100° C. After epihalohydrin addition is completed, the reactants are heated for at least an additional 30 minutes at a temperature of about 100° C. so as to obtain complete reaction. As required, additional catalyst may be added so as to enhance the reaction rate leading to final and complete reaction of all reactants. Additional epihalohydrin may be added so as to increase the mole ratio of the final product obtained through this reaction. When the preferred adduct is obtained, such as, the adduct represented by Formulas I or II above, the phosphonation reaction may be commenced in the same autoclave or may be commenced by cooling the autoclave contents, isolating the contents or a portion thereof, and reacting this product with one of the appropriate phosphonating agents or phosphonate containing reactants hereinafter described.

Reaction Conditions, The Amine Reaction

The reaction between the perfluoro alcohol/oxirane-substituted oxirane/epihalohydrin adduct and the amine may be conducted using any of the well known methods as well as any other method which results in the desired reaction.

The epihalohydrin adduct of the oxirane substituted perfluoro alcohol is isolated and added to a reaction vessel containing an excess of an equimolar amount of an aqueous solution of ammonia or a desired amine and the mixture is stirred at ambient temperature for about one hour. The epihalohydrin adduct is diluted to about a 50 percent active solution utilizing a 50:50 mixture by weight of an alcohol and water. This procedure produces an amine through dehydrohalogenation and amine addition.

Reaction Conditions, Synthesis of Phosphonates

The phosphonates may be produced by a number of various techniques which are known by the art. In one method, a Mannich-type reaction is effected utilizing the previously described amines, formaldehyde and phosphorous acid. The reaction proceeds according to the general formula:

$$RNH_2 + 2CH_2O + 2HP(O)(OH)_2 \rightarrow RN[CH_2P(O)(OH)_2]_2 + H_2O$$

wherein R represents either the described alkyl radicals or perfluoro-substituted radicals of the present invention. The reaction proceeds equally well with primary amines or polyamines. Optimum yields are achieved when the reaction is effected at a pH level below 7 and the reaction mixture is heated to reflux temperature for several hours. A further description of a suitable method of preparing phosphonates utilizing amino compounds is set forth in U.S. Pat. No. 3,269,812 and U.S. Pat. No. 3,288,846, the entire disclosures of which are incorporated herein by reference.

EXAMPLES FOR COMPOUNDS OF FORMULA I

EXAMPLE 1

Into a conventional jacketed, glass-lined mixing vessel fitted with a water condenser are charged 164 parts of orthophosphorous acid, 102 parts of n-hexylamine, and 50 parts of water. The resulting mixture is stirred continuously through the remainder of the process described below. The mixture is heated to 95° C., and maintained at about 95° C. while, over a period of about 20 minutes, 66 parts (10% excess) of paraformaldehyde are added slowly thereinto. Then, for an additional hour after all the formaldehyde has been added, the resulting mixture is refluxed at a temperature of about 110° C., after which time to reaction mixture is cooled to room temperature. It is found that more than 90% of the orthophosphorous acid is converted to the desired product, hexylaminodi(methylphosphonic acid), $C_6H_{13}N(CH_2PO(OH)_2)_2$.

EXAMPLE 2

Into a mixing vessel such as that described in Example 1, above, are charged 164 parts of orthophosphorous acid, 213 parts of n-tetradecylamine, and 50 parts of water. The resulting mixture is stirred continuously through the remainder of the process described below. The mixture is heated to 95° C., and maintained at about 95° C. while, over a period of about 20 minutes, 66 parts (10% excess) of paraformaldehyde are added slowly thereinto. Then for an additional hour after all the formaldehyde has been added, the resulting mixture is refluxed as a temperature of about 110° C. after which the reaction mixture is cooled to room temperature. It is found that more than 90% of the orthophosphorous acid is converted to the desired product, n-tetradecylamino-di-(methylphosphonic acid), $C_{14}H_{29}N(CH_2PO(OH)_2)_2$.

EXMAPLE 3

Into a mixing vessel similar to that described in Example I above, are charged 164 parts of orthophosphorous acid, 266 parts of oleylamine, and 50 parts of water. The resulting mixture is stirred continuously through the remainder of the process described below. The mixture is heated to 95° C., and maintained at about 95° C. while, over a period of about 20 minutes, 66 parts (10% excess) of paraformaldehyde are added slowly thereinto. Then for an additional hour after all formaldehyde has been added, the resulting mixture is refluxed at a temperature of about 110° C. after which the reaction mixture is cooled to room temperature. It is found that more than 90% of the orthophosphorous acid is converted to the desired product, oleylaminodi(methylphosphonic acid), $C_{18}H_{35}-NH_2 \rightarrow C_{18}H_{35}N(CH_2PO(OH)_2)_2$.

EXMAPLES FOR COMPOUNDS OF FORMULA II

I. Alkoxylates-the formation of the initial adduct between the perfluoro alcohol and the oxirane/substituted oxirane compounds.

A. Ethylene Oxide (EO)

EXMAPLE 4

To a PARR autoclave is added 485 grams (1 mole) Zonyl BA alcohol and 1 cc of antimony pentachloride. The autoclave was closed and heated to 50° C. Three hundred fifty-two (352) grams (approximately 8 moles) of ethylene oxide was slowly added to the autoclave, the addition rate being controlled in such a manner as to maintain the reaction temperature below 100° C. After at least ½ of the EO was added, the addition rate was increased in such a manner as to allow the reaction temperature to slowly rise to 140° C. After the addition of ethylene oxide was completed, the autoclave temperature was maintained at 130°-140° C. for one hour. The contents of the autoclave were then cooled and removed from the autoclave. The reaction product is the alkoxylate expected from the addition of 8 moles of ethylene oxide to 1 mole of the Zonyl BA perfluoro alcohol.

EXMAPLE 5

Four hundred eighty-five (485) grams of the Zonyl BA alcohol and 1 cc of antimony pentachloride was added to an autoclave and heated to 50° C. Four hundred forty (440) grams (10 moles) of EO was added slowly so as to maintain reaction temperature below 100° C. Reaction temperature may be controlled by the addition rate of EO or by adjusting the rate of cooling of the PARR autoclave using external cooling coils. After about ⅓ of the ethylene oxide was added, the reaction temperature was allowed to rise to 140C. After the addition of EO was completed, the reaction vessel temperature was maintained between 130°-140° C. for approximately one hour by heating this reaction vessel. The contents were cooled and removed from the autoclave. The reaction product is that expected from the 10 mole addition of ethylene oxide to the Zonyl BA perfluoro alcohol previously described.

EXMAPLE 6

The conditions of Examples 1 and 2 were repeated except that 15 moles of ethylene oxide were added at such a rate as to control the reaction temperature below 140° C. The product mix obtained was that expected from the 15 mole addition of ethylene oxide to the perfluoro alcohol.

B. Propylene Oxide (PO)

EXMAPLE 7

To an autoclave was added 485 grams (1 mole) of the Zonyl BA perfluoro alcohol. The autoclave was purged with nitrogen and 2 cc of antimony pentachloride was added. The autoclave was closed to the atmosphere and heated to 50° C. while stirring. Two moles (about 108 grams) of PO was slowly added to the reaction vessel at a rate sufficient to maintain the reaction temperature below 100° C. Addition of the propylene oxide required approximately one hour. The autoclave contents were then heated for another hour at a temperature of 90° C. The reactor was cooled and approximately 666 grams of this 2 mole adduct of the perfluoro alcohol/propylene oxide alkoxylated was removed for further reaction.

EXMAPLE 8

To the materials remaining in the autoclave from Example 7 was added 108 grams of propylene oxide. The initial temperature at the start of the reaction was 52° C. The vessel was depressurized and another 0.5 mls of antimony pentachloride catalyst was added. Addition of the propylene oxide was reinitiated. The temperture of the reaction vessel was less than 80° C. throughout the addition of propylene oxide. The heat source was wurned off and the autoclave allowed to cool overnight. The next day, the contents of the autoclave were determined to be the 4 mole adduct of propylene oxide of the perfluoro alcohol.

EXMAPLE 9

Three hundred (300) grams of the alkoxylate adduct obtained from Example 7 was charged to a PARR autoclave along with 0.06 cc of antimony pentachloride. The reactor was purged with nitrogen and heated to 50° C. Addition of propylene oxide was begun. Sufficient propylene oxide was added to the reactor to obtain a 6 mole propylene oxide adduct onto the perfluoro alcohol. The propylene oxide addition rate was maintained so as to control the reaction temperature below 100° C. during the addition of propylene oxide. The reaction vessel was heated for an additional hour after the addition of propylene oxide was completed at a temperature of 100° C. The reaction vessel was cooled and the 6 mole propylene oxide adduct of the perfluoro alcohol was removed from the reactor.

EXMAPLE 10

Three hundred (300) grams of the adduct from Example 7 was charged to a PARR autoclave along with 1 milliliter of antimony pentachloride. The same precautions were taken as in Example 9 to maintain reaction temperatures and to maintain a nitrogen atmosphere. Sufficient propylene oxide was added to obtain a 10 mole propylene oxide adduct of the Zonyl BA perfluoro alcohol.

C. Mixed Oxide Alkoxylate

EXMAPLE 11

To a PARR autoclave was added 485 grams (1 mole) perfluoro alcohol and 2 millilites of antimony pentachloride. The reactor was purged with nitrogen and closed to the atmosphere. The reactor contents were heated to 50° C. while they were being stirred. Ten moles of ethylene oxide were slowly added to the reactor contents at a rate sufficient to maintain the temperature of the reactor below 100° C. The reactor was heated at a temperature of 100° C. for 1.5 hours after the addition of all of the ethylene oxide. After this heating period, 5 moles of propylene oxide were slowly added so as to maintain the reactor temperature at 100° C. The reactor contents were then agitated for an additional hour and the temperature was allowed to rise slowly to 130° C. The temperature was maintained at 130°C. for an hour after all the ethylene oxidehad been added. The autoclave was cooled and approximately 1,220 grams of the final alkoxylate adduct were recovered, demonstrating essentially 100% recovery.

II. The Reaction Between Alkoxylates and Epihalohydrin

EXMAPLE 12

To an autoclave was added 485 grams of Zonyl BA perfluoro alcohol and 2 milliliters of antimony pentachloride catalyst. The autoclave was purged with nitrogen and closed to the atmosphere. The autoclave was heated to 60°-70° C. for about 30 minutes. A mixture of 330grams of ethylene oxide and 442 grams of propylene oxide was slowly added to the stirred contents of the autoclave. The addition rate of this mixed oxide solution was controlled such that the temperature never exceeded 90° C. and, in fact, remained in the 75°-85° C. range. The temperature was maintained for about 90 minutes after the addition of the mixed oxide was complete.

To the contents of the PARR autoclave was then added 170 grams or approximately 1.5 moles of eichlorohydrin. The same reaction conditions and temperature ranges were maintained as above. An additional 60 minutes of reaction time was allowed after the audition of epichlorohydrin was complete so as to complete the reaction between the epichlorohydrin and the mixed alkoxylate obtained in the previous reaction step.

EXMAPLE 13

Two hundred four (204) grams of an 8 mole EO adduct of the Zonyl BA perfluoro alcohol and 0.25 milliliter of BF$_3$ etherate were placed in a 500 milliliter flask. The flask was equipped with a condenser, a stirrer, a thermometer, and a pressure equalized dropping funnel This mixture was heated to 50° C. and a nitrogen purge was initiated. Dropwise addition of epichlorohydrin was started. The reaction temperature was held between 55°–60° C. by regulating the rate of addition of epichlorohydrin. Approximately 34.5 grams of epichlorohydrin was added to the flask contents over a period of one hour. The reaction contents were postheated for approximately 1.5 hours, then cooled and removed from the flask. The product was an adduct of the perfluoro alcohol/8 mole ethylene oxide/1.5 mole epichlorohydrin. Product yield as judged by the weight of recovered material is 98+%.

EXMAPLE 14

Into 3 separated flasks equipped as in Example 13, products from Section I.B., Examples 7, 8 and 9[were independently charged. Sufficient BF$_3$ etherate was added to the contents of each flask and the flasks heated to approximately 50° C. Nitrogen purges were started on each flask. Epichlorohydrin was added to each flask so as to yield a 2 mole epichlorohydrin adduct to the materials obtained from Example 4, and a 1.5 mole epichlorohydrin adduct from both the materials of Examples 5 and 6. The epichlorohydrin was added at a rate which maintained the temperature of each reaction vessel at less than 95° C. Again each reaction vessel was postheated for approximately one hour at temperatures not exceeding 95° C. The products obtained in each case were respectively those expected from (1) 1:2:2 mole adduct of perfluoro alcohol/propylene oxide/epichlorohydrin; (2) a 1:4:1.5 mole adduct of perfluoro alcohol/propylene oxide/epichlorohydrin; and (3) a 1:6:1.5 mole adduct of perfluoro alcohol/propylene oxide/epichlorohydrin adduct.

EXMAPLE 15

One mole of a product obtained from following the first step of Example 12 is added to a 500 ml flask equipped as above. Sufficient epibromohydrin to obtain a 1 mole adduct is slowly added to this material after it is heated to approximately 50° C. and 1 milliliter of antimony pentoxide is added to the flask. The epibromohydrin addition rate is controlled such that the reaction temperature never exceeds 100° C. The product expected is a 1:2:2:1.0 molar adduct of perfluoro alcohol/ethylene oxide/propylene oxide/ and epibromohydrin.

III. The Amine Reaction

EXMAPLE 16

To a reaction vessel containing an excess of aqueous ammonia is added the 8 mole ethylene oxide epichlorohydrin adduct of Zonyl BA perfluoro alcohol of Example 13. The adduct is dissolved in a 50:50 mixture by weight of isopropanol and water in an amount sufficient to provide a 33 percent active solution. The mixture is stirred for several hours while being refluxed. The resulting product is found to be the amine of the 8 mole ethylene oxide, epi adduct of Zonyl BA perfluoro alcohol.

EXMAPLE 17

To a reaction vessel was added the 8 mole ethylene oxide epichlorohydrin adduct of Zonyl BA perfluoro alcohol of Example 13. The adduct was diluted as in Example 16. To the diluted mixture is added a slight excess of ethylene diamine after which the mixture is stirred at 0° to 10° C. for several hours. The resulting product is found to be the diamine of the 8 mole ethylene oxide epichlorohydrin adduct of Zonyl BA perfluoro alcohol. IV. The Phosphonate Reaction

EXMAPLE 18

To a mixing vessel as described in Example 1 is added one mole of the amine product of Example 16, 164 parts by weight of orthophosphorous acid and 50 parts of water. The mixture is stirred continuously through the remainder of the process. The mixture is heated to 95° C. and maintained at about 95° C. over a period of about 20 minutes during which 66 parts of formaldehyde is slowly added.

Then, the mixture is refluxed at a temperature of about 110° C. for an additional hour after which the mixture is cooled to room temperature. It is found that a substantial portion of the mixture has been converted to the desired phosphonate product.

EXMAPLE 19

To a mixing vessel as described in Example 1 is added one mole of the amine product of Example 17, 164 parts by weight of orthophosphorous acid and 50 parts of water. The mixture is stirred continuously while being heated to 95° C. at which time 66 parts of formaldehyde is slowly added. Then, the mixture is refluxed at a temperature of about 110° C. for about one hour after which the mixture is cooled to room temperature. It is found that a substantial portion of the mixture has been converted to the desired phosphonate product.

EXAMPLE 20

To illustrate the effectiveness of the compositions of the present invention in enhancing hydrocarbons permeability in a limestone matrix and improving the return of treating fluids by lowering capillary pressure, the following tests were performed. The tests utilize a dolomite column which is treated with fluids containing the composition of the present invention in an amount of about 0.2 percent by weight and a conventional fluid comprising 2 percent KCl. The percent treating fluid recovered at hydrocarbon breakthrough is measured and the water saturation of the dolomite column. The treatment with 2% KCl results in about a 28 percent recovery of treating fluid at oil breakthrough in the column while the use of the composition of the present invention in a 0.2 percent concentration provides about 100 percent recovery of treating fluid at oil breakthrough.

Test Procedure

A packed column having a ¾" O.D. and about 12 in. length is prepared with sieved 100-200 mesh dolomite and placed in the test sytem illustrated in the drawing. API standard brine is flowed into the packed column at a rate of 1.0 cc/min until the column is saturated. The time required to achieve saturation is about 10 minutes. The pore volume of the packed column then is determined by well known techniques.

Thereafter, a refined hydrocarbon oil is flowed through the packed column in the reverse direction to prior brine flow at a rate of 1.0 cc/min to obtain a residual water saturation level within the column. Thereafter, one pore volume of the treating fluid containing 0.2 percent by weight of the designated composition of the present invention is flowed into the column in the same direction as the previously introduced brine at a rate of 1 cc/min. The treating fluid also contained 2% KCl and a nonemulsifier consisting of an alhoxylated phenol formaldehyde resin and various ethoxylated components. A quantity of the refined oil then is flowed in the opposite direction of the treating fluid at various rates as set forth in the following table for two hours at each rate. The volume of brine and treating fluid recovered and the pressure is measured at each of the various flow rates as well as the percent of the treating fluid recovered at oil breakthrough. The equilibrium water saturation within the packed column and the relative oil permeability then are calculated at each oil flow rate by known techniques.

The effectiveness of the various compounds of the present invention in lowering capillary pressure and improving aqueous treatment fluid recovery and hydrocarbon permeability in limestone matrices is summarized in Table 1, below.

TABLE I

Water Recovery and Capillary Pressure Measurements Employing Perfluoro-Substituted Phosphonates

| Composition | Water Recovery at Oil Breakthrough (% Treatment Fluid) | (Sw) | Capillary Oil Flow (cc/min) | Pressure Data ($\Delta P$) | (Sw) |
|---|---|---|---|---|---|
| 2% KCl | 28 | 72 | 0.5 | 1.56 | 71.0 |
|  |  |  | 1.0 | 2.32 | 63.7 |
|  |  |  | 5.0 | 8.42 | 38.2 |
|  |  |  | 10.0 | 15.62 | 32.0 |
| Diphosphonate of octyl amine (Formula I) | 100 | 39 | 1.0 | 4.5 | 37.0 |
| Diphosphonate of perfluoro-substituted amine (Formula II) | 100 | 47 | 1.0 | 4.0 | 41.0 |

While particular embodiments of the invention have been described, it is to be understood that such descriptions are presented for purposes of illustration only and that the invention is not limited thereto and that reasonable variations and modifications, which will be apparent to those skilled in the art, can be made without departing from the spirit or scope of the invention as defined by the following claims.

What is claimed is:

1. A method of increasing the production of hydrocarbons from a hydrocarbon-containing subterranean carbonate-containing formation comprising contacting said formation with an anionic compound whereby said compound is absorbed onto surfaces of said formation to reduce wetting of said surfaces by either hydrocarbons or water, said anionic compound being selected from individual compounds and mixtures thereof represented by the formulas:

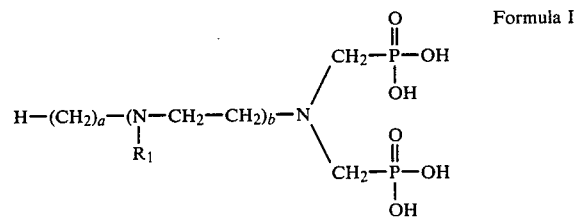

Formula I or

-continued

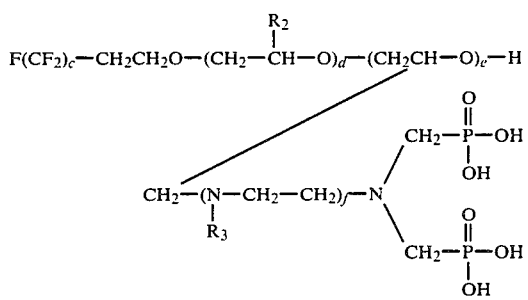
Formula II wherein a is a whole number or fraction thereof in the range of from about 4 to about 18;
wherein b is a whole number or fraction thereof in the range of from about 1 to about 5;
wherein c is a whole number or fraction thereof in the range of from about 4 to about 18;
wherein d is a whole number or fraction thereof in the range of from about 0 to about 29;
wherein e is a whole number or fraction thereof in the range of from about 1 to about 3;
wherein f is a whole number or fraction thereof in the range of from about 0 to about 9;
$R_1$ is independently selected from the group consisting of hydrogen, a methyl group or methyl phosphonate;
$R_2$ is independently selected from the group consisting of hydrogen, a methyl group and an ethyl group; and
$R_3$ is independently selected from the group consisting of hydrogen, a methyl group or methyl phosphonate.

2. The method of claim 1 wherein said contacting of said formation with said anionic compound is brought about by dissolving or dispersing said compound in a carrier fluid and introducing said carrier fluid into said formation.

3. The method of claim 1 wherein:
a is from about 8 to 10;
b is from about 1 to 3;
c is from about 6 to 12;
d is from about 1 to 25;
e is from about 1 to about 2; and
f is from about 1 to about 6.

4. The method of claim 1 wherein said contacting of said formation with said anionic compound is brought about by dissolving or dispersing said compound in a carrier fluid and introducing said carrier fluid into said formation, said anionic compound being present in an amount of from about 0.01 to about 0.5 percent by weight of said carrier fluid.

5. In a mjethod of fracturing a subterranean hydrocarbon-containing formation containing carbonates to stimulate the production of hydrocarbons therefrom wherein a fracturing fluid is introduced into said formation in a manner whereby fractures are created therein, the improvement comprising:
combining with said fracturing fluid an anionic compound having the property of absorbing on surfaces of said formation whereby wetting of said surfaces by either hydrocarbons or water is reduced, said anionic compound being selected from individual compounds and mixtures thereof represented by the formulas:

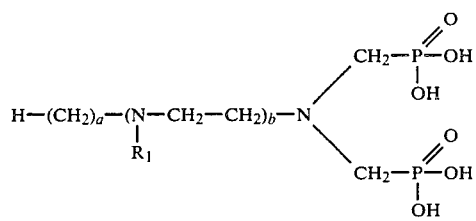
Formula I or

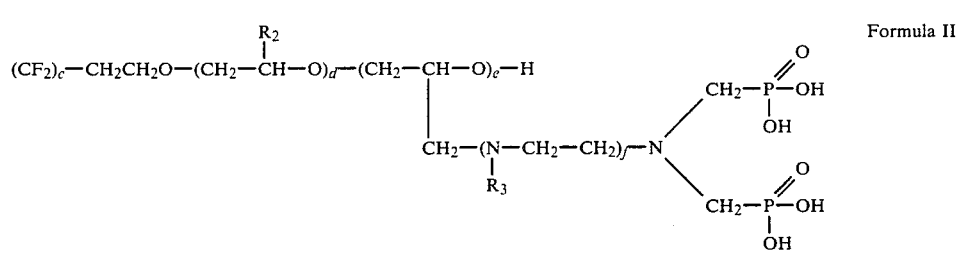
Formula II wherein a is a whole number or fraction thereof in the range of from about 4 to about 18;
wherein b is a whole number or fraction thereof in the range of from about 1 to about 5;
wherein c is a whole number or fraction thereof in the range of from about 4 to about 18;
wherein d is a whole number or fraction thereof in the range of from about 0 to about 29;
wherein e is a whole number or fraction thereof in the range of from about 1 to about 3;
wherein f is a whole number or fraction thereof in the range of from about 0 to about 9;
$R_1$ is independently selected from the group consisting of hydrogen, a methyl group or methyl phosphonate;
$R_2$ is independently selected from the group conisting of hydrogen; a methyl group and an ethyl group; and
$R_3$ is independently selected from the group consisting of hydrogen, a methyl group or methyl phosphonate.

6. The method of claim 5 wherein:
a is from about 8 to 10;
b is from about 1 to 3;

c is from about 6 to 12;
d is from about 1 to 25;
e is from about 1 to about 2; and
f is from about 1 to about 6.

7. The method of claim 5 wherein said anionic compound is present in said fracturing fluid in an amount of from about 0.01 to about 0.5 percent by weight of said fracturing fluid.

8. A method of increasing the production of hydrocarbons from a hydrocarbon-containing subterranean carbonate-containing formation comprising contacting said formation with an anionic perfluoro-substituted compound whereby said compound is absorbed onto surfaces of said formation to reduce wetting of said surfaces by either hydrocarbons or water, said anionic perfluorosubstituted compound being selected from individual compounds and mixtures thereof represented by the formula:

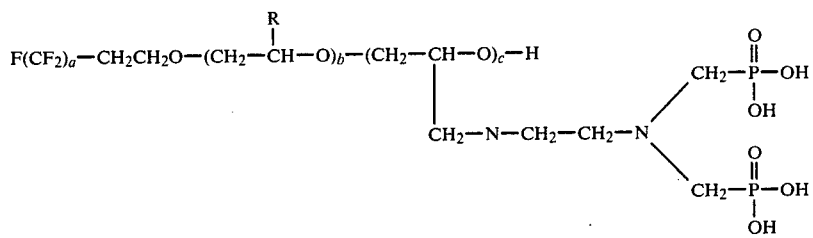

wherein a is a whole number or fraction thereof in the range of from about 6 to about 12;

b is a whole number or fraction thereof in the range of from about 10 to about 25;

c is a whole number or fraction thereof in the range of from about 1 to about 2; and R is independently selected from hydrogen and methyl radicals.

9. The method of claim 8 wherein:
a is from about 7 to about 9;
b is from about 15 to about 25;
c is from about 1 to about 3.

* * * * *